United States Patent
Brechtel et al.

(10) Patent No.: US 10,295,460 B2
(45) Date of Patent: May 21, 2019

(54) LASER-BASED IR SPECTROSCOPY FOR MEASURING SULFUR TRIOXIDE IN THE EXHAUST GAS OF GAS POWER PLANTS

(71) Applicant: Siemens Aktiengesellschaft, Munich (DE)

(72) Inventors: Kevin Brechtel, Uehlfeld (DE); Katrin Raake, Rödermark (DE); Henning Schramm, Hofheim am Taunus (DE); Ralf Sigling, Baiersdorf (DE); Rainer Strzoda, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 15/556,741

(22) PCT Filed: Feb. 23, 2016

(86) PCT No.: PCT/EP2016/053773
§ 371 (c)(1),
(2) Date: Sep. 8, 2017

(87) PCT Pub. No.: WO2016/146351
PCT Pub. Date: Sep. 22, 2016

(65) Prior Publication Data
US 2018/0059013 A1    Mar. 1, 2018

(30) Foreign Application Priority Data
Mar. 18, 2015   (DE) .................. 10 2015 204 883

(51) Int. Cl.
*G01N 33/00* (2006.01)
*G01N 21/3518* (2014.01)
(Continued)

(52) U.S. Cl.
CPC ......... *G01N 21/3518* (2013.01); *G01N 21/39* (2013.01); *G01N 33/0042* (2013.01);
(Continued)

(58) Field of Classification Search
CPC ............... G01N 21/3518; G01N 21/39; G01N 33/0042; G01N 21/031; G01N 2021/391
See application file for complete search history.

(56) References Cited

U.S. PATENT DOCUMENTS 4,542,621 A   9/1985 Andersson et al.
4,976,100 A   12/1990 Lee
(Continued)

FOREIGN PATENT DOCUMENTS

DE   69013981 T2   3/1995
EP   2437046 A1   4/2012
(Continued)

OTHER PUBLICATIONS

International Search Report dated May 10, 2016, for PCT/EP2016/053773.
(Continued)

*Primary Examiner* — David P Porta
*Assistant Examiner* — Djura Malevic
(74) *Attorney, Agent, or Firm* — Beusse Wolter Sanks & Maire

(57) ABSTRACT

A method for determining a sulfur trioxide content in a gas. A sample of the gas is taken, and a gas pressure of the sample is reduced. A wave number-resolved transmission measurement is carried out on the sample using a wave number-tunable monochrome light source, and a sulfur trioxide content is derived from the measurement. The measurement is carried out in the sulfur trioxide absorption band between 1360 and 1410 $cm^{-1}$, in particular in a window around the sulfur trioxide absorption at 1365.49 $cm^{-1}$. A method for
(Continued)

operating a power plant, a measuring system for determining a sulfur trioxide content in a gas, and a power plant are adapted to determine a sulfur trioxide content in a gas.

20 Claims, 3 Drawing Sheets

(51) Int. Cl.
  *G01N 21/39* (2006.01)
  *G01N 21/3504* (2014.01)
  *G01N 21/03* (2006.01)
(52) U.S. Cl.
  CPC ....... *G01N 21/031* (2013.01); *G01N 21/3504* (2013.01); *G01N 2021/391* (2013.01); *G01N 2021/399* (2013.01)

(56) References Cited

U.S. PATENT DOCUMENTS

| | | | | |
|---|---|---|---|---|
| 5,458,010 A | * | 10/1995 | Traina | G05D 11/03 73/864.12 |
| 5,567,226 A | * | 10/1996 | Lookman | B03C 3/013 110/345 |
| 8,368,896 B1 | | 2/2013 | Li et al. | |
| 2003/0184320 A1 | * | 10/2003 | Breen | G01N 17/02 324/691 |
| 2010/0037678 A1 | * | 2/2010 | Chothani | G01N 27/14 73/25.01 |
| 2011/0045422 A1 | * | 2/2011 | Tanca | F23D 1/02 431/76 |
| 2011/0097809 A1 | * | 4/2011 | Evans | G01N 33/0042 436/102 |
| 2012/0075632 A1 | | 3/2012 | Baasner et al. | |
| 2012/0113426 A1 | | 5/2012 | Rao | |
| 2013/0332084 A1 | | 12/2013 | Boonefaes | |

FOREIGN PATENT DOCUMENTS

| | | | |
|---|---|---|---|
| JP | S59157419 A | | 9/1984 |
| JP | 2001188040 A | | 7/2001 |
| JP | 2001348211 A | | 12/2001 |
| JP | 2003014637 A | * | 1/2003 |
| JP | 2013061358 A | | 4/2013 |
| JP | 2014512517 A | | 5/2014 |

OTHER PUBLICATIONS

IPPR (PCT/IPEA/416 and 409) dated Feb. 14, 2017, for PCT/EP2016/053773.

Majkowski Richard F et al, "Infrared absorption coefficients of gaseous H(2)SO(4) and SO(3)", Applied Optics, vol. 17, No. 7, pp. 975-977, ISSN: 0003-6935, DOI: 10.1364/ao.17.000975, Washington DC (US).

Dene C et al, EPRI Project Manager, Technical Report "Continuous Measurement Technologies for SO(3) and H(2)SO(4) in Coal-fired Power Plants", 1009812, Final Report, 104 pgs, Sep. 2004, Palo Alto CA (US).

Rawlins W T et al., Optical Society of America, Laser Diagnostics for Gasdynamics, "A Quantum Cascade Laser Sensor for SO(2) and SO(3) for Application to Combustor Exhaust Streams"; Applied Optics, vol. 44, No. 31, pp. 6635-6643, 33 pgs, Nov. 2005, Physical Sciences Inc, Andover MA (US), http://www.psicorp.com/pdf/library/sr-1210.pdf.

Socha Jeff et al, Thermo Fisher Scientific, "Thermo Scientific Sulfur Trioxide CEMS Development", http://www.ayt.cl/files/articulos/WP_AQISO3_0810.pdf; 2010, White Paper, 3 pgs, Franklin MA (US).

Geosyntec Consultants, Technology Brief, "Advanced Real Time Monitoring of SO(2), SO(3), H(2)O and NH(3)", 4 pgs, Charlotte NC (US), http://practices.geosyntec.com/air-quality/pdf/Geosyntec-SO3-Analyzer-Technical-Brief.pdf.

Rawlins Wilson T et al, Optical Society of America, "Quantum cascade laser sensor for SO(2) and SO(3) for application to combustor exhaust streams"; Applied Optics; vol. 44, No. 31, pp. 6635-6643; XP001236488; ISSN: 0003-6935; DOI: 10.1364/A0.44.006635, Nov. 2005, Washington DC (US).

Anto P L et al: "Spectroscopic investigations and computational study of sulfur trioxide-pyridine complex"; Journal of Raman Spectroscopy; vol. 42, pp. 1812-1819, Research Article; wileyonlinelibrary.com; DOI 10.1002/jrs.2928; 2011.

Central Research Institute of Electric Power Industry: "Development of SOx measurement technology in flue gas exhaust gas using infrared laser spectroscopy"; Report of the Central Research Institute of Infrared Laser Power: Report number: H08006; Apr. 2009.

* cited by examiner

LASER-BASED IR SPECTROSCOPY FOR MEASURING SULFUR TRIOXIDE IN THE EXHAUST GAS OF GAS POWER PLANTS

CROSS REFERENCE TO RELATED APPLICATIONS

This application is the US National Stage of International Application No. PCT/EP2016/053773 filed Feb. 23, 2016, and claims the benefit thereof. The International Application claims the benefit of German Application No. DE 102015204883.7 filed Mar 18, 2015. All of the applications are incorporated by reference herein in their entirety.

FIELD OF INVENTION

The invention relates to a method for determining a sulfur trioxide content in a gas and a method for operating a power plant with a gas turbine and with a heat recovery steam generator. The invention further relates to a measuring system for determining a sulfur trioxide content in a gas, and a power plant with a gas turbine and a heat recovery steam generator.

BACKGROUND OF INVENTION

Normally, natural gas contains only very small amounts of sulfur (S). It is assumed that the sulfur content in the combustion gas for a gas turbine is completely converted to sulfur dioxide ($SO_2$) during the combustion process with oxygen ($O_2$).

$$S + O_2 \rightarrow SO_2$$

In the gas flow of the heat recovery steam generator, sulfur dioxide is partially further converted to sulfur trioxide ($SO_3$):

$$SO_2 + \tfrac{1}{2} O_2 \rightarrow SO_3.$$

The resulting sulfur dioxide—and sulfur trioxide concentrations in the exhaust gas are in any case initially comparatively small. Nevertheless, the sulfur trioxide concentration should be determined or at least estimated with regard to possible sulfuric acid formation and its negative effects on the cold end of a heat recovery steam generator of a gas and steam turbine plant, because sulfur trioxide reacts with water ($H_2O$) to give sulfuric acid ($H_2SO_4$):

$$SO_3 + H_2O \rightarrow H_2SO_4$$

The sulfuric acid condenses on falling below the sulfuric acid dew point and leads to corrosion. A determining or estimation of the sulfur trioxide content is not entirely simple, however, because the conversion rate is a function of various parameters.

For example, in units with catalysts for the selective catalytic reaction or with catalysts for carbon monoxide, the sulfur dioxide conversion increases at these catalysts; the sulfur trioxide concentration is therefore increased.

A further factor which is to be taken into consideration is the dwell time of the exhaust gas in the heat recovery steam generator, which fluctuates depending on a gas turbine load. The lower the gas turbine load, the longer the dwell time of the exhaust gas also is in the heat recovery steam generator and consequently the conversion of sulfur dioxide to sulfur trioxide also increases.

A provision for the prevention of sulfuric acid is to ensure that the temperature of the condensate preheater in the heat recovery steam generator lies permanently above the sulfuric acid dew point.

In the interests of as high an efficiency of the plant as possible, the temperature of the condensate preheater should, however, be as low as possible.

It is therefore common practice for gas and steam turbine plants to carry out an estimation of the sulfur dioxide conversion rate, which will be rather more conservative with regard to corrosion problems and at the expense of efficiency. For this, the minimum temperature of the waste gas in the heat recovery steam generator of a gas and steam turbine power plant is selected, through corresponding design of the heat recovery steam generator and a correspondingly high condensate flow temperature, to be so high that sufficient reliability is present in order to in any case not fall below the acid dew point of the sulfuric acid (e.g. 10 K over the expected dew point). Through the "safety distance", the exhaust gas in the heat recovery steam generator is not cooled to an extent as would be theoretically possible without the occurrence of sulfuric acid corrosion. Hereby, if applicable, heat is "given away" in the region of several MW, the efficiency of the gas and steam turbine power plant reduces. It would therefore be desirable to be able to determine the sulfur trioxide content in the exhaust gas more precisely.

The sulfur trioxide content or respectively sulfuric acid content of the exhaust gas can take place through sampling and chemical analysis in the laboratory. However, such a method is slow, laborious and expensive [Continuous Measurement Technologies for $SO_3$ and $H_2SO_4$ in Coal-Fired Power Plants, EPRI, Palo Alto, Calif.: 2004. 1009812.].

The sulfur content in coal leads, in coal-fired power plants, to sulfur trioxide concentrations in the exhaust gas of 1 to 100 ppm. For this concentration range, probes exist which determine the sulfuric acid content in situ by the method of controlled condensation [Continuous Measurement Technologies for $SO_3$ and $H_2SO_4$ in Coal-Fired Power Plants, EPRI, Palo Alto, Calif.: 2004. 1009812.].

For the same concentration range, there is also an approach of measuring in situ by means of laser spectroscopy directly in the exhaust gas [http://practices.geosyntec.com/air-quality/pdf/Geosyntec-SO3-Analyzer-Technical-Brief.pdf]. Extractive methods with laser spectroscopy are also known. The methods are, however, limited hitherto to comparatively high sulfur trioxide concentrations (0.5 ppm-200 ppm) [http://www.psicorp.com/pdf/library/sr-1210.pdf], [http://www.ayt.cl/files/articulos/WP_AQISO3_0810.pdf], [U.S. Pat. No. 8,368,896 B1].

The sulfur trioxide concentrations which are expected in the exhaust gas of a gas-operated power plant lie in the range of 10 to 1000 ppb.

SUMMARY OF INVENTION

It is therefore an object of the invention to indicate a method for determining a sulfur trioxide content in a gas, in particular in an exhaust gas of a gas turbine, so that the temperature at the cold end of a heat recovery steam generator can be kept as low as possible, in order to increase the efficiency of a power plant. A further object of the invention is to indicate a method for operating a power plant with a gas turbine and with a heat recovery steam generator. Furthermore, it is an object of the invention to indicate a corresponding measuring system for determining a sulfur trioxide content in a gas or respectively a corresponding power plant.

The invention solves the problem directed to a method for determining a sulfur trioxide content in a gas by making provision that in such a method, in which a sample of the gas is taken and a gas pressure of the sample is reduced, and with a wave number tunable monochrome light source a wave number resolved transmission measurement is carried out on the sample and from the measurement a sulfur trioxide content is derived, the measurement takes place in the sulfur trioxide absorption band between 1360 and 1410 cm$^{-1}$, in particular in a window around the sulfur trioxide absorption at 1365.49 cm$^{-1}$.

The spectroscopy is typically applied with tunable semiconductor lasers. A wave number resolved transmission measurement is carried out with the tunable light source. The transmitted light is picked up by a photodetector.

The spectral measurement takes place in an extractive system, i.e. a sample is taken from the gas and is delivered to a measuring cell. In the measuring cell, the gas is kept at a reduced pressure in order to reduce the line width of the absorption lines and thereby in the first place to enable the separation of the spectra of the individual gases. At normal pressure, the water absorption overlies the majority of the sulfur trioxide band and thus prevents a selective measurement of the sulfur trioxide concentration in the low concentration range.

The use of the sulfur trioxide absorption at 1365.49 cm$^{-1}$ in connection with a reduced pressure in the absorption measuring cell offers a range of advantages. The measurement takes place in a spectral gap of the water spectrum, i.e. the spectral range is largely transparent. In the gap, the absorption of the target gas and of further exhaust gas components occur.

The absorption of sulfur trioxide in the target wave number window has, compared to the neighboring lines, a greater amplitude by at least the factor 2 and a narrower shape than those of the adjacent sulfur trioxide absorptions. The greater absorption facilitates the realization of a low detection limit, the narrow line facilitates the selection with respect to the potentially interfering absorptions of the other exhaust gas components. The remaining exhaust gas components in the occurring concentration range lead only to a slight interference of the sulfur trioxide spectrum.

In order to reduce the line width of the absorption lines and thereby in the first place to enable the separation of the spectra of the individual gases, it is necessary to keep the gas in the measuring cell at a reduced pressure. In particular, it is advantageous if the sample is brought to a pressure below 100 hPa.

With regard to the line intensity determined by the Boltzmann distribution and the density of state and therefore also with regard to the detection limit, it is advantageous in the case of the sulfur trioxide absorption at 1365.49 cm–1 if a sample temperature above the dew point of sulfuric acid, for example at 200° C., is set.

It is, furthermore, advantageous, if the measurement takes place by means of wavelength modulation spectroscopy (WMS) with detection of the $2^{nd}$ harmonic (or also higher harmonics), because this technology minimizes the influence of neighboring lines on the spectrum of the target gas. In particular, a partial overlap of the absorption line of sulfur trioxide with sulfur dioxide occurs. The application of wavelength modulation spectroscopy with optimum setting of the modulation amplitude suppresses the sulfur dioxide absorption in favor of the sulfur trioxide line.

It is expedient here if the spectral measurement is carried out in a long path cell with a multiply folded beam path, in particular if an absorption section is a maximum of 15 m, advantageously a maximum of 10 m, in particular a maximum of 5 m. Thereby, with the target absorption line at 1365.49 cm$^{-1}$, an absorption is reached at 1 ppm in the 1% range.

It is, furthermore, expedient if a measured spectrum is compared in a curve fitting with a model spectrum, and the concentration of sulfur trioxide enters as parameter into the model spectrum.

In addition, it is expedient if in addition to the concentration of sulfur trioxide, concentrations of interfering gases also enter into the model either as known values which originate from a second independent measurement method, or as fit parameters.

The problem directed to a method for operating a power plant with a gas turbine and a heat recovery steam generator is solved in that a sulfur trioxide content in the exhaust gas of the gas turbine is determined and an exhaust gas temperature in the heat recovery steam generator is adapted on the basis of the sulfur trioxide content so that a sulfuric acid dew point is not fallen below in the heat recovery steam generator.

The problem directed to a measuring system for determining a sulfur trioxide content in a gas is solved by a measuring system for determining a sulfur trioxide content in a gas, comprising a first gas line from a gas take-off point to a measuring cell, a pressure regulation device for the measuring cell, a wave number tunable monochrome light source in the region of a sulfur trioxide absorption band, a control for carrying out a transmission measurement in the measuring cell, and an evaluation unit for determining the sulfur trioxide content, wherein the light source is suited to generate monochromatic light between 1360 and 1410 cm$^{-1}$, in particular in a window around the sulfur trioxide absorption at 1365.49 cm$^{-1}$.

In an advantageous embodiment of the invention, the pressure regulation device comprises a pressure regulator and a vacuum pump, which are connected to the measuring cell via a second gas line.

In a further advantageous embodiment, at least one of the two, first gas line and measuring cell, is heatable. Therefore, with the selected wave number, the line intensity can be increased with respect to ambient temperature or respectively the temperature at the branch-off point, and the accuracy of detection of sulfur trioxide can be improved.

In order to keep particles away from the measuring system, it is advantageous if the measuring system comprises a particle filter connected into the first gas line.

Expediently, the measuring system comprises a throttle device connected into the first gas line. The throttle device follows the filter in the direction of flow of the gas. The throttle device can be a simple throttle or alternatively a mass flow controller, which provides the desired throughput at underpressure operation.

In an advantageous embodiment of the invention, the measuring cell is a long path cell with a multiply folded beam path, which has an absorption section of 5 to 15 m, advantageously 7 to 12 m.

According to the invention, a power plant with a gas turbine and a heat recovery steam generator also comprises such a measuring system.

In contrast to the method disclosed in U.S. Pat. No. 8,368,896 B1, which uses the absorption of sulfur trioxide at 1397 cm$^{-1}$, which is also largely uninfluenced by the sulfur dioxide concentration at sulfur dioxide concentrations >100 ppm, the absorption at 1365.49 cm$^{-1}$ of the method according to the invention has a partial overlap with the sulfur dioxide absorption. This means that both gas components must be taken into consideration in the evaluation, in order to compensate the cross-influence. However, this also means that both components can be detected and quantitatively evaluated in a single spectral measurement. The problem is alleviated in the target wave number window in that a further sulfur dioxide absorption occurs separately from the sulfur trioxide absorption (between 1365.52 and 1365.54 $cm^{-1}$) and thereby an independent sulfur dioxide measurement is made possible, which facilitates the evaluation.

Owing to the intensity of the sulfur dioxide absorption in relation to the sulfur trioxide absorption, the measuring method is best suited for natural gas-fired power plants in which only sulfur dioxide concentrations<5 ppm occur. The measuring method is also able to be used for oil-fired power plants, in which sulfur dioxide concentrations<50 ppm occur. For coal-fired power plants with sulfur dioxide concentrations>100 ppm, the accuracy of the sulfur trioxide measurement will decrease, because the correction of the sulfur trioxide absorption with the sulfur dioxide absorption becomes more difficult.

With regard to absorption intensity, the absorption of sulfur trioxide at 1365.49 $cm^{-1}$ is superior to the absorption of sulfur trioxide at 1397 $cm^{-1}$, which militates in favor of the choice of the 1365.49 $cm^{-1}$ absorption for applications with a detection limit in the ppb range. U.S. Pat. No. 8,368,896 B1 discloses an absorption of the lines with a measuring cell length of 12 m and 1 ppm sulfur trioxide at 443 K in the low per mille range. The simulation of the absorption intensity with the data of the HITRAN database (abbreviation for "High Resolution Transmission", a collection of spectroscopic parameters for the simulation of transmission and emission, maintained by the Harvard-Smithsonian Center for Astrophysics, Cambridge Mass., USA) produces for ambient temperature an absorption intensity of around 1%. The data of the HITRAN database do not permit for sulfur trioxide the calculation of the spectra at increased temperature. An estimation with the available data produces at 200° C. an increase in the absorption by a factor of 2 to 3. This means that the absorption intensity between the absorption at 1365.49 $cm^{-1}$ and the range around 1397 $cm^{-1}$ differs by an order of magnitude which affects the detection sensitivity which is able to be achieved.

In contrast to previous calculations/estimations of the sulfur trioxide content in the waste gas and the corresponding design/operation of the heat recovery steam generator with considerable safety margins the sulfur trioxide concentration in the waste gas is now measured directly and is used for the setting/regulating of the condensate flow temperature.

Through the use of the measurement for a regulation of the condensate flow temperature, the waste gas in the heat recovery steam generator can now be cooled substantially further, whereby more steam can be generated. The efficiency of the gas and steam turbine power plant increases. Furthermore, through a regulating of the condensate flow temperature it is ensured that the temperature of the exhaust gas always lies above the acid dew point and acid corrosion can thus not occur. This means an increased safety compared to the previous procedure, (because safety margins with very inaccurate estimation of the sulfur trioxide concentration offer no guarantee that the margin was also high enough— e.g. in the case of chronological fluctuations of the sulfur content in the combustion gas of the gas turbine, wherein this is only guaranteed to the operator generally as a monthly average.

An adapting of the exhaust gas temperature accurate to the minute would be possible and all the more effective (with regard to corrosion safety and power plant efficiency), because in recent times different/fluctuating gas qualities (Russia, Norway, North Sea, USA, . . . ) are coming into use increasingly.

The flexibility of the power plant increases, because with corresponding knowledge concerning the sulfur trioxide concentration in the exhaust gas (particularly in the case of partial load the $SO_2 \rightarrow SO_3$ conversion rate is difficult to predict without measurement) the control of the power plant can be acted upon with corresponding provisions.

BRIEF DESCRIPTION OF THE DRAWINGS

The invention is explained in further detail by way of example with the aid of the drawings. There are shown diagrammatically and not to scale.

DETAILED DESCRIPTION OF INVENTION

Figure 1:
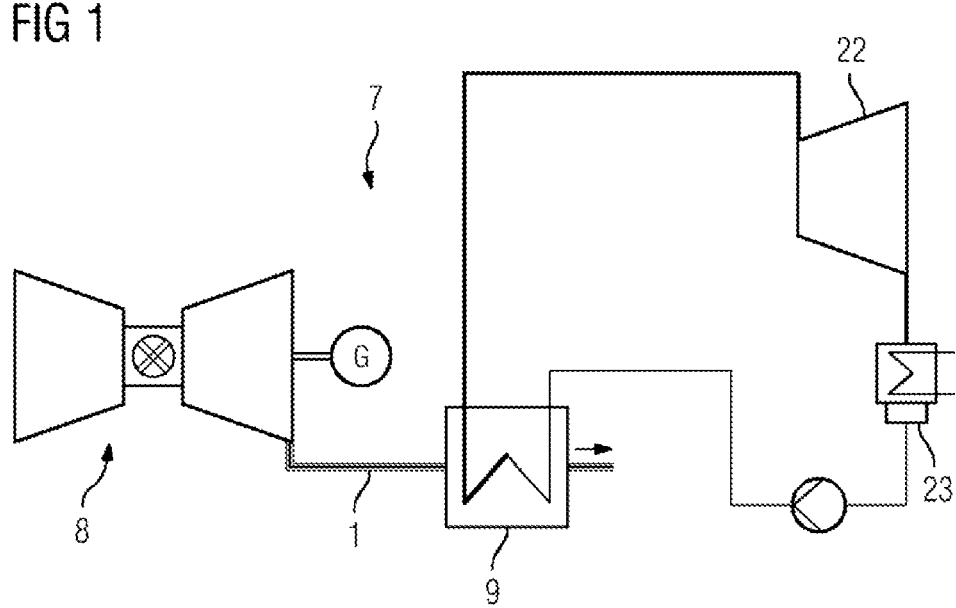
FIG. 1 a gas and steam turbine plant.

FIG. 1 shows diagrammatically and by way of example a power plant 7, in particular a gas and steam turbine plant. Steam for the operation of the steam turbine 22 is generated by the exhaust gas 1 of the gas turbine 8 in the heat recovery steam generator 9 downstream of the gas turbine 8. Steam which is expanded in the steam turbine 22 is condensed in the condenser 23 and is delivered again to the heat recovery steam generator 9.

Figure 2:
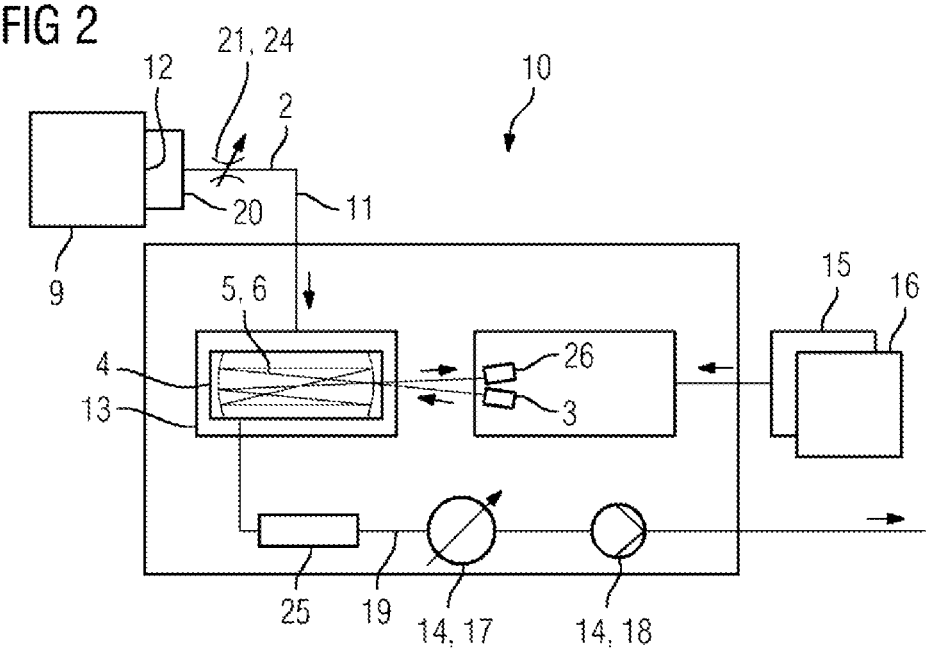
FIG. 2 a measuring system according to the invention.

FIG. 2 shows a measuring system 10 according to the invention. The gas take-off takes place at the heat recovery steam generator 9 at a suitable gas take-off point 12 (at the point at which the lowest temperature is to be expected). In order to keep particles away from the measuring system 10, the sample 2 (i.e. the measurement gas) passes firstly through a particle filter 20 with adapted pore size, which withstands the operating conditions at the place of use. A possibility would be a PTFE filter, which is temperature-stable up to 260° C. and is supplied with various pore sizes. Following the filter 20 is a throttle device 21, for example a simple throttle or alternatively a mass flow controller 24, which provides the desired throughput at underpressure operation. A first gas line 11 from the gas take-off point 12 to the measuring cell 13 should be flexible, owing to the thermal expansion of the heat recovery steam generator 9, able to be heated to 200° C. and embodied to be as short as possible, in order to keep the dwell time of the sample 2 small. The greater the ratio of surface to volume of the first gas line 11, the greater is the risk that interaction between sample 2 and surface such as adsorption or catalytic conversion processes take place to an interfering extent. Inert surfaces further reduce the interactions. Teflon pipes are approved for the transport of measurement gases, if concentrations in the sub-ppm range are to be measured. Alternatively, high-grade steel surfaces can be provided with a silicon dioxide coating, which reduces the interaction with the surface. As the spectroscopy does not require a drying of the sample 2, a gas conditioning is dispensed with. Thereby, a further source for a falsification of the gas composition is eliminated. From the heated first gas line 11, the sample 2 is directed into the likewise heated measuring cell 13. The required absorption section 6 (approximately 10 m) is provided by a long path cell 4 for a multiply folded beam path 5. After the measuring cell 13, the sample 2 is cooled in a gas cooler 25, which is connected into a second gas line 19, to temperatures which are compatible for the pressure regulator 17 of a pressure regulation device 14. The pressure regulator 17 keeps the pressure in the measuring cell 13 constant at low pressure (e.g. 100 hPa), the pressure at which the spectral line widths are so small that the individual absorption lines can be separated. A vacuum pump 18 generates the underpressure required for the operation of the pressure regulator 17. For the examination of the sample 2 in the measuring cell 13, a wave number tunable monochrome light source 3 (laser), a photodiode 26, and in addition a control 15 for carrying out a transmission measurement and an evaluation unit 16 are required.

Figure 3:
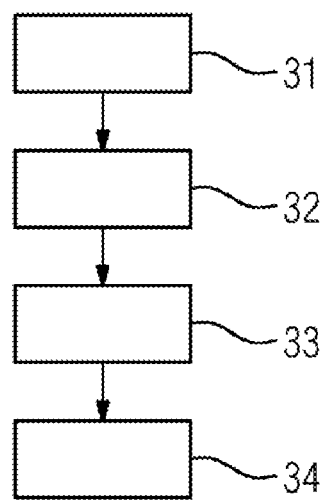
FIG. 3 the method for determining a sulfur trioxide content in a gas according to the invention and FIG. 4 a WMS spectrum ($2^{nd}$ harmonic) of sulfur trioxide and sulfur dioxide around 1365.5 $cm^{-1}$.

FIG. 3 shows the method for determining a sulfur trioxide content in a gas, in which in a first step 31 a sample 2 of the gas 1 is taken and in a second step 32 a gas pressure of the sample 2 is reduced, and in a third step 33 with a wave number tunable monochrome light source 3 on the sample 2 a wave number resolved transmission measurement is carried out in the sulfur trioxide absorption band between 1360 and 1410 $cm^{-1}$, in particular in a window around the sulfur trioxide absorption at 1365.49 $cm^{-1}$ and in a fourth step 34 a sulfur trioxide content is derived from the measurement.

Figure 4:
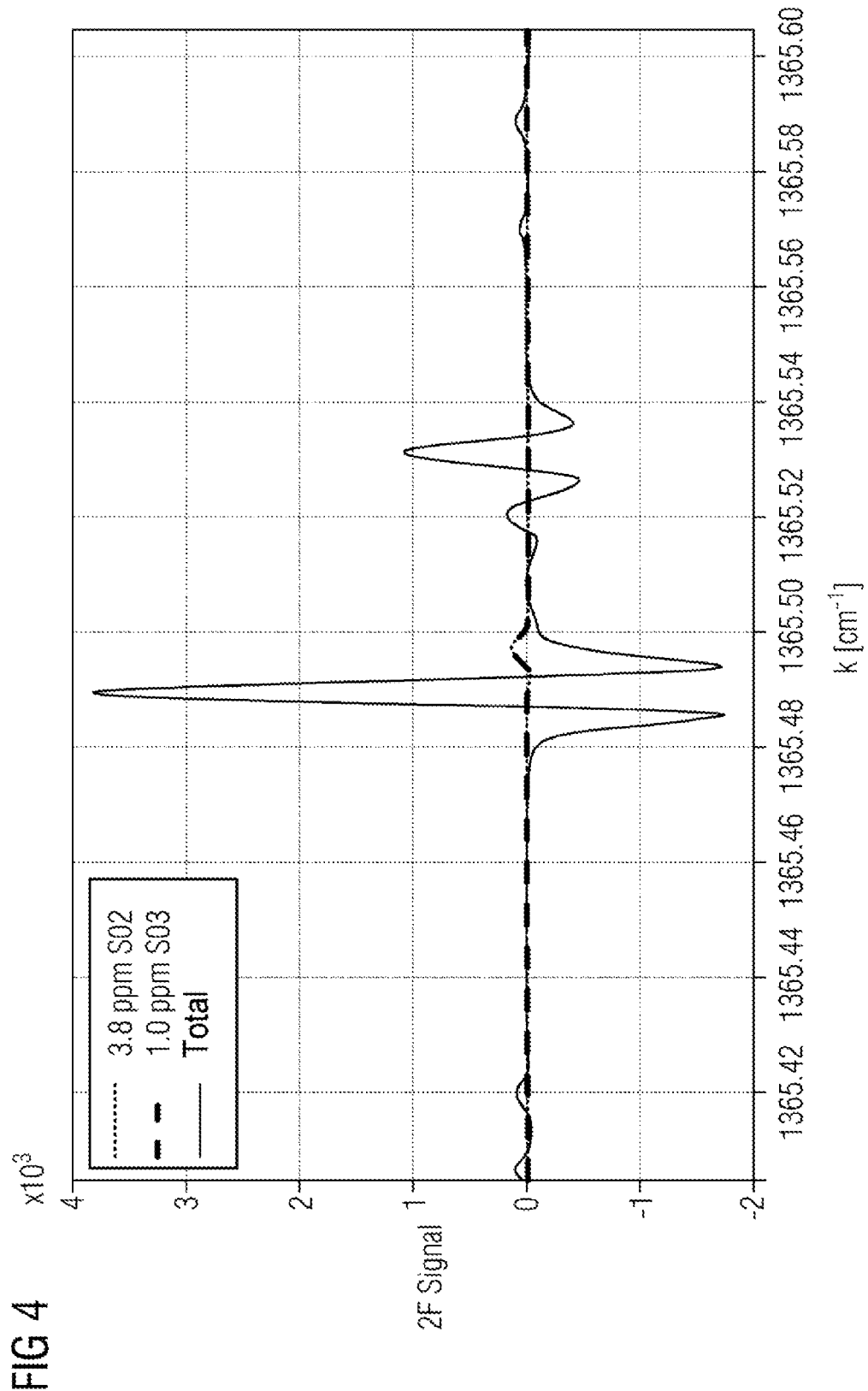

FIG. 4 shows a wavelength modulation spectrum ($2^{nd}$ harmonic) of sulfur trioxide and sulfur dioxide around 1365.5 $cm^{-1}$. The wavelength modulation spectroscopy method practically completely eliminates the influence of the water absorption in the region of the sulfur trioxide absorption.

The invention claimed is:

1. A method for determining a sulfur trioxide content in a combustion gas also containing sulfur dioxide and water, comprising:
   taking a sample of a gas comprising sulfur dioxide at <50 ppm and reducing a gas pressure of the sample, and
   with a wave number tunable monochrome light source, carrying out a wave number resolved transmission measurement on the sample and from the measurement deriving a sulfur trioxide content,
   wherein the measurement is a single spectral measurement in a window around 1365.5 $cm^{-1}$, and
   the sulfur trioxide content is derived by compensating sulfur trioxide absorption at 1365.49 $cm^{-1}$ for a cross-influence of sulfur dioxide absorption between 1365.52 and 1365.54 $cm^{-1}$.

2. The method as claimed in claim 1, wherein the sample is brought to a pressure below 100 hPa.

3. The method as claimed in claim 1, wherein a sample temperature above 200° C. is set.

4. The method as claimed in claim 1, wherein the measurement takes place by wave length modulation spectroscopy (WMS) with detection of the 2nd harmonic or else higher harmonics.

5. The method as claimed in claim 1, wherein the spectral measurement is carried out in a long path cell with a multiply folded beam path.

6. The method as claimed in claim 5, wherein an absorption section is a maximum of 15 m.

7. The method as claimed in claim 1, wherein a measured spectrum is compared in a curve fitting with a model spectrum, and the concentration of sulfur trioxide enters as parameter into the model spectrum.

8. The method as claimed in claim 7, wherein in addition to the concentration of sulfur trioxide, concentrations of interfering gases also enter into the model either as known values which originate from a second independent measuring method, or as fit parameters.

9. A method for operating a power plant with a gas turbine and with a heat recovery steam generator, the method comprising:
   determining a sulfur trioxide content in combustion exhaust gas of the gas turbine as claimed in claim 1, and
   adapting an exhaust gas temperature in the heat recovery steam generator on the basis of the sulfur trioxide content so that a sulfuric acid dew point is not fallen below in the heat recovery steam generator.

10. A measuring system for determining a sulfur trioxide content in a combustion gas also containing sulfur dioxide at <50 ppm and water, comprising:
    a first gas line from a gas take-off point to a measuring cell,
    a pressure regulation device for the measuring cell,
    a wave number tunable monochrome light source in the region of a sulfur trioxide absorption band,
    a control for carrying out a transmission measurement in the measuring cell, and
    an evaluation unit for determining the sulfur trioxide content,
    wherein the light source is suited to generate monochromatic light in a window around 1365.5 $cm^{-1}$, and
    the evaluation unit determines the sulfur trioxide content by compensating sulfur trioxide absorption at 1365.49 $cm^{-1}$ for a cross-influence of sulfur dioxide absorption between 1365.52 and 1365.54 $cm^{-1}$.

11. The measuring system as claimed in claim 10, wherein the pressure regulation device comprises a pressure regulator and a vacuum pump, which are connected to the measuring cell via a second gas line.

12. The measuring system as claimed in claim 10, wherein at least one of the two, first gas line and measuring cell, is heatable.

13. The measuring system as claimed in claim 10, further comprising a particle filter connected into the first gas line.

14. The measuring system as claimed in claim 10, further comprising a throttle device connected into the first gas line.

15. The measuring system as claimed in claim 10, wherein the measuring cell is a long path cell with a multiply folded beam path, which has an absorption section of 5 to 15 m.

16. A power plant comprising:
    a gas turbine,
    a heat recovery steam generator, and
    a measuring system as claimed in claim 10.

17. The method as claimed in claim 5, wherein an absorption section is a maximum of 10 m.

18. The method as claimed in claim 5, wherein an absorption section is a maximum of 5 m.

19. The measuring system as claimed in claim 15, wherein the absorption section is 7 to 12 m.

20. The method as claimed in claim 9, further comprising adapting the exhaust gas temperature in the heat recovery steam generator so that the sulfuric acid dew point is not fallen below by regulating a condensate flow temperature in response to the determined sulfur trioxide content.

* * * * *